(12) United States Patent
Becourt et al.

(10) Patent No.: US 7,138,138 B2
(45) Date of Patent: Nov. 21, 2006

(54) PHARMACEUTICAL FORMULATION HAVING A MASKED TASTE AND METHOD FOR THE PRODUCTION THEREOF

(75) Inventors: Philippe Becourt, Massy (FR); Josiane Chauvin, Montge en Goele (FR); Detlev Schwabe, Hofheim (DE)

(73) Assignee: Aventis Pharma S.A., Antony (FR)

( * ) Notice: Subject to any disclaimer, the term of this patent is extended or adjusted under 35 U.S.C. 154(b) by 514 days.

(21) Appl. No.: 10/735,538

(22) Filed: Dec. 12, 2003

(65) Prior Publication Data

US 2004/0142029 A1 Jul. 22, 2004

Related U.S. Application Data

(63) Continuation of application No. PCT/FR02/02158, filed on Jun. 21, 2002.

(30) Foreign Application Priority Data

Jun. 21, 2001 (FR) .................................. 01 08157

(51) Int. Cl.
*A61K 9/20* (2006.01)
*A61K 9/26* (2006.01)
*A61K 9/14* (2006.01)

(52) U.S. Cl. ...................... 424/465; 424/464; 424/469; 424/489

(58) Field of Classification Search ................. None
See application file for complete search history.

(56) References Cited

U.S. PATENT DOCUMENTS 5,084,278 A * 1/1992 Mehta

FOREIGN PATENT DOCUMENTS

| EP | 0293885 | 12/1988 |
|----|---------|---------|
| JP | 63-150220 | 6/1988 |
| WO | WO 99/17742 | 4/1999 |

* cited by examiner

*Primary Examiner*—Humera N. Sheikh
(74) *Attorney, Agent, or Firm*—Balaram Gupta

(57) ABSTRACT

The invention relates to a pharmaceutical formulation in the form of a powder which is administered orally in an aqueous suspension, having a masked taste, and comprising at least one cellulose polymer, a methacrylic polymer and an active ingredient which is distributed in a homogeneous manner in a molecular state in an atomized matrix, in addition to an alkaline agent and an adsorbing agent, a method for the production thereof and a method for masking the taste of pharmaceutical products.

20 Claims, No Drawings

PHARMACEUTICAL FORMULATION HAVING A MASKED TASTE AND METHOD FOR THE PRODUCTION THEREOF

This application is a continuation of International application No. PCT/FR02/02,158, filed Jun. 21, 2002; which claims the benefit of priority of French Patent Application No. 01/08,157, filed Jun. 21, 2001.

A subject of the present invention is a pharmaceutical formulation in the form of a powder intended for oral administration in an aqueous suspension, having a masked taste, a process for its preparation and a method for masking the taste of pharmaceutical products.

It is well known that numerous pharmaceutical products intended for oral administration have a very unpleasant taste and sometimes a very high persistence. This is the case in particular with antibiotic products commonly called by the name of macrolides or macrolide-like, such as ketolides, or of cephalosporins or quinolones. This of course assumes a particular importance in the case where the said pharmaceutical products are intended to be administered to children.

Several processes for masking the taste of pharmaceutical products have been described in the literature. These processes most often consist of covering the microparticles of products with a film which disappears after passage through the mouth. There may be mentioned, for example, the article by Roy "Taste masking in oral pharmaceuticals", Pharmaceutical Technology—April 1994—p. 84–99 or the Patent Application WO 98/14179. There are also processes in which the active materials are included in materials which allow their release in the body under defined conditions. Such matrices are described, for example, by C. Brossard in Actualites Pharmaceutiques—No. 388—July–August 2000, or in the Patent Applications WO 99/08660, WO 99/17742 or EP 1027887.

One problem to be solved in the case of a matrix is to ensure that the bioavailability of the active material included in a matrix remains acceptable, taking into account the fact that the components (excluding the active ingredient) of the matrix which can be used are not necessarily favorable, for various inherent reasons.

A subject of the present invention is a pharmaceutical formulation having a masked taste, the masking of which persists during administration of the formulation, in particular in the form of a suspension in an aqueous vehicle, characterized in that it comprises at least the following elements:
a)—a cellulosic polymer which is soluble in organic solvents but practically insoluble in water, regardless of the pH;
a methacrylic polymer which is soluble in an acid medium and practically insoluble at a neutral or alkaline pH and
an active ingredient distributed in a homogeneous manner and in the molecular state in the mixture, which is in the form of an atomized matrix;
b)—an alkaline agent of an organic nature, or an alkaline salt, which is pharmaceutically acceptable;
c)—an adsorbent agent.

As indicated above, the formulation according to the invention is intended to be suspended in water and then, where appropriate, stored in this state for some days, in practice 5 to 10 days, during its absorption period.

It is important to note that each of the three elements of the formulation cooperates with the other two, but that the entirety of the three elements, however, is essential to obtain the required effect of masking the taste at the time of absorption of the formulation according to the invention.

In a non-limiting manner, the various constituents of the formulation according to the invention, which must of course be pharmaceutically acceptable, can be chosen as follows:

The cellulosic polymer is, in particular, ethylcellulose. It must be soluble in the organic solvents used in the process according to the invention and as insoluble as possible in water, regardless of the pH.

The methacrylic polymer must be soluble in water at an acidic pH (5 or less than 5) and as insoluble as possible at a neutral and alkaline pH, and its function is firstly to ensure that only the relatively small proportion of the active ingredient present on the surface of the microparticles which make up the formulation are accessible to dissolution after being suspended in water for the purpose of absorption, and secondly to ensure a good bioavailability of the active ingredient after its ingestion. It is chosen, in particular, from polymers which are known by the name Eudragit E and are available from the company Rohm Pharma GmbH, these being cationic polymers formed from 2-dimethylaminoethyl methacrylate and neutral methacrylates.

The alkaline agent ensures an alkaline pH in the formulation after suspension thereof in water for the purpose of its absorption, and ensures that the majority of the active ingredient dispersed in the matrix remains inaccessible to dissolution after suspension in water. In acting in this manner, it contributes towards limiting the unpleasant taste. It is chosen, in particular, from the group consisting of meglumine, lysine and sodium and potassium citrate and carbonate.

The adsorbent agent ensures adsorption on its surface of the amounts of active ingredient released after suspension of the formulation in water, while allowing its release in the stomach and thus ensuring its good bioavailability. In acting in this manner, it also contributes towards limiting the unpleasant taste. It is chosen, in particular, from talc and magnesium aluminum silicate, the latter being more particularly preferred, in particular in a fine particle size.

The active ingredient can be, in particular, an antibiotic of the macrolide or macrolide-like type, that is to say erythromycin and its derivatives, such as, for example, roxithromycin, telithromycin, azithromycin or clarithromycin, or of the cephalosporin, penicillin, tetracycline or quinolone type, but also any other type of substance administered orally and having an unpleasant taste which is required to be masked, as long as it has a sufficient solubility in the organic solvent used in the preparation of the formulation.

A particular subject of the present invention is a formulation as defined above, characterized in that the active ingredient is an antibiotic of the macrolide or macrolide-like type such as those mentioned above, and more particularly, a ketolide such as telithromycin. This compound is described, for example, in European Patent EP 0 680 967.

The cellulosic polymer is present in the atomized matrix in a proportion which preferably ranges from 30% to 50% by weight, and the methacrylic polymer is present in a proportion of 10% to 25% by weight. The active ingredient is present in the atomized matrix at a maximum level of 50% by weight.

A more particular subject of the present invention is a formulation as defined above, characterized in that the proportions of cellulosic and methacrylic polymers in the matrix range respectively from 40% to 45% and from 15% to 20% by weight, and in that the proportion of the active ingredient in the matrix ranges up to 30% by weight.

It is acknowledged that for a product such as telithromycin, a concentration of 10 µl/ml is already unacceptable because of its unpleasant taste and its very high persistence. Taking into account the significant amount of the active ingredient which is present on the surface of the microparticles of the matrix and which consequently is accessible to dissolution, that is to say an amount which is very much greater than the 10 µl/ml above, it is thus surprising that masking of the taste is obtained by entraining of the active ingredient in the matrix.

The formulation according to the invention can also comprise one or more other elements known individually to a person skilled in the art, in particular a hydrophobic plasticizing agent and an antioxidant agent, as regards the matrix itself, and one or more preservative agents, one or more sweetening agents, a thickening agent, and one or more flavoring agents.

The above elements can be chosen, in particular, as follows:

The hydrophobic plasticizing agent is, for example, dibutyl sebacate or diethyl phthalate.

The antioxidant agent is, for example, α-tocopherol, BHT or 2,6-di-tert-butyl-4-methylphenol or BHA or 2-tert-butyl-4-methoxyphenol.

The preservative agent is, for example, methyl or propyl parahydroxybenzoate.

The sweetening agent or agents are chosen from those which are usually used in the pharmaceuticals or foodstuffs industry, for example maltitol, sodium saccharinate or saccharose.

The thickening agent is, for example, a xanthan gum or the sodium salt of carboxymethylcellulose.

The flavoring agent or agents are chosen from those which are usually used in the pharmaceuticals or foodstuffs industry.

It is known that a compound such as ethylcellulose which is insoluble in water, regardless of the pH, if present inside a matrix reduces the bioavailability of the active ingredient by impeding its diffusion towards the mucous membranes where it is absorbed.

It is also known that an adsorbent agent such as magnesium aluminum silicate also reduces the bioavailability of an active ingredient due to the potent adsorption effect which manifests itself on its surface (see, for example, Handbook of Pharmaceutical Excipients p. 269–273,7, 11 and 12 (1994)).

A person skilled in the art therefore should not be prompted to use such compounds to formulate an active ingredient under the conditions of the invention.

Generally speaking, the beneficial effect of masking of taste obtained by means of the use in pharmaceutical formulations of such compounds should thus logically be adversely affected by the reduced bioavailability of the active ingredient, and it should thus be expected that the formulation according to the invention has a delayed effect as regards the therapeutic efficacy of the active ingredient. In fact, this is not the case and, unexpectedly, the formulation on the contrary demonstrates a very good in vivo bioavailability of the active ingredient while masking the bad taste in amounts which are quite remarkable.

It has thus been found in tests in vivo that the bioavailability can range from 60 to 100% in the case of traditional tablets, and indeed can be better with a proportion which can reach about 30%.

A subject of the present invention is also a process for the preparation of a pharmaceutical formulation as defined above, characterized in that a cellulosic polymer and a methacrylic polymer as defined above and, where appropriate, a plasticizing agent and an antioxidant agent as defined above are mixed in an organic solvent, the active ingredient is then added, the solution obtained is then passed through an atomizer to obtain a powder in the form of an atomized matrix, the said powder is mixed with an alkaline agent and an adsorbent agent as defined above and, where appropriate, with one or more elements chosen from the group consisting of preservative agents, sweetening agents, thickening agents and flavoring agents as defined above, and the expected formulation is obtained.

The organic solvent is chosen such that it is a good solvent simultaneously for the cellulosic polymer, the methacrylic polymer, the active ingredient and, where appropriate, the plasticizing and antioxidant agents. It is thus possible to use, in particular, solvents such as halogenated hydrocarbons, in particular methylene chloride, alcohols, in particular ethanol and isopropanol, and ketones, in particular acetone and methyl ethyl ketone.

A subject of the present invention is also a process for masking the taste of a pharmaceutical active ingredient intended for oral administration in an aqueous suspension, characterized in that the said active ingredient is entrained homogeneously inside a matrix comprising at least a cellulosic polymer and a methacrylic polymer as defined above and is combined there with at least an alkaline agent and an adsorbent agent as defined above.

The following example illustrates the invention, without however limiting it:

1 Preparation of a Solution for Atomization

The following starting ingredients are used:

| Composition | g | 1 batch (g) |
| --- | --- | --- |
| Telithromycin | 30.0 | 1,050.0 |
| Eudragit E 100 ® | 18.0 | 630.0 |
| Ethylcellulose N10 | 44.0 | 1,540 |
| Dibutyl sebacate | 7.50 | 262.5 |
| α-Tocopherol | 0.50 | 17.5 |
| Methylene chloride q.s. | 1,000 | 35,000 |

The procedure is as follows:

The dibutyl sebacate, α-tocopherol, Eudragit E 100® and ethylcellulose N10 are introduced into 20 liters of methylene chloride with moderate agitation. Agitation is continued overnight.

One hour before the start of the atomization, the telithromycin is dissolved in the solution of polymers and the solution is made up to the desired weight with methylene chloride.

2 Atomization

The operation is carried out in an atomizer in accordance with the following parameters:

Inlet temperature: 85° C.

Outlet temperature: 45–55° C.

Two-fluid or single-fluid nozzle

The nozzle and the drying chamber are placed entirely under nitrogen.

3 Secondary Drying

The atomization product is spread out on plates and placed in an oven under a flow of nitrogen at room temperature for 24 hours.

An atomization product comprising 30% active ingredient is finally obtained.

4 Preparation of the Final Mixture

| Composition | g/bottle | For 2,000 bottles (g) |
|---|---|---|
| Atomization product with 30% telithromycin | 8.334 | 16,668 |
| Meglumine | 0.400 | 800 |
| Veegum (F) ® (1) | 2.000 | 4,000 |
| Rhodigel ultra ® (2) | 0.025 | 50 |
| Maltitol P 90 (3) | 13.526 | 27,052 |
| Methyl p-hydroxybenzoate | 0.100 | 200 |
| Propyl p-hydroxybenzoate | 0.015 | 30 |
| Sodium saccharinate | 0.300 | 600 |
| Strawberry flavor (05) | 0.300 | 600 |

(1) Magnesium aluminium silicate of fine particle size.
(2) Xanthum gum
(3) P 80 designates a particular particle size of the maltitol.

A so-called "return" mixer is used.

Before the products are introduced into the mixer, they are passed through a sieve with a mesh opening of 850 μm. Mixing is then carried out as follows:

Premixing: all the excipients and only ⅓ of the maltitol are mixed for 10 minutes at 20 rpm;

Mixing: the remainder of the maltitol and the atomization product are then mixed for 30 minutes at 20 rpm.

The final mixture is then distributed into the bottles.

It should be noted that the names Eudragit E, Veegum F and Rhodigel ultra are registered trademarks.

The invention claimed is:

1. A pharmaceutical formulation having a masked taste, the masking of which persists during administration of the formulation, in particular, in the form of a suspension in an aqueous vehicle, comprising:

a)—a cellulosic polymer which is soluble in organic solvents but practically insoluble in water, regardless of the pH;

a methacrylic polymer which is soluble in an acid medium and practically insoluble at a neutral or alkaline pH and an active ingredient distributed in a homogeneous manner and in the molecular state in the mixture, which is in the form of an atomized matrix;

b) a pharmaceutically acceptable alkaline agent of an organic nature or an alkaline salt; and c) an adsorbent agent, wherein the cellulosic polymer and the methacrylic polymer are respectively ethylcellulose in an amount of from about 30% to about 50% by weight and a cationic polymer formed from 2-dimethylaminoethyl methacrylate and neutral methacrylates in an amount of from about 10% to about 25% by weight and wherein the alkaline agent and the adsorbent agent are respectively selected from the group consisting of meglumine, lysine, sodium and potassium citrate and sodium and potassium carbonate, and selected from the group consisting of magnesium aluminum silicate and talc.

2. The formulation according to claim 1 wherein the alkaline agent and the adsorbent agent are respectively meglumine and magnesium aluminum silicate.

3. The formulation according to claim 1 wherein the active ingredient is an antibiotic of the macrolide or macrolide-like, cephalosporin, penicillin, tetracycline or quinolone type.

4. The formulation according to claim 3, wherein the active ingredient is telithromycin.

5. The formulation according to claim 1 wherein:

the cellulosic polymer is present in the atomized matrix in a proportion ranging from about 30% to about 50% by weight and the methacrylic polymer is present in a proportion ranging from about 10% to about 25% by weight; and the active ingredient is present in the atomized matrix at a maximum level of about 50% by weight.

6. The formulation according to claim 5, wherein the proportions of cellulosic and methacrylic polymers in the matrix range respectively from about 40% to about 45% and from about 15% to about 20% by weight, and in that the maximum amount of the active ingredient in the matrix is about 30% by weight.

7. The formulation according to claim 1 which also comprises within the matrix a hydrophobic plasticizing agent and/or an antioxidant agent.

8. The formulation according to claim 1 which further comprises one or more elements chosen from preservative agents, sweetening agents, thickening agents and flavoring agents.

9. A process for the preparation of a pharmaceutical formulation according to claim 1 comprising:

mixing a cellulosic polymer and a methacrylic polymer and, optionally, a hydrophobic plasticizing agent and an antioxidant agent in an organic solvent;

adding the active ingredient to the above mixture;

passing the solution thus obtained through an atomizer in order to obtain a product in the form of an atomized matrix; and mixing the product with an alkaline agent and an adsorbent agent, optionally, with one or more elements chosen from the group consisting of preservative agents, sweetening agents, thickening agents and flavoring agents.

10. The process according to claim 9 wherein the organic solvent used is chosen from the group consisting of halogenated hydrocarbons, alcohols and ketones.

11. The process according to claim 10 wherein the solvent is methylene chloride.

12. The process according to claim 9 wherein the cellulosic polymer is soluble in organic solvents but practically insoluble in water, regardless of the pH;

and the methacrylic polymer is soluble in an acid medium and practically insoluble at a neutral or alkaline pH.

13. The process according to claim 12 wherein the cellulosic polymer and the methacrylic polymer are respectively ethylcellulose and a cationic polymer formed from 2-dimethylaminoethyl methacrylate and neutral methacrylates.

14. The process according to claim 9 wherein the active ingredient is an antibiotic of the macrolide or macrolide-like, cephalosporin, penicillin, tetracycline or quinolone type.

15. The process according to claim 14 wherein the active ingredient is telithromycin.

16. The process according to claim 9 wherein the alkaline agent and the adsorbent agent are chosen respectively from the group consisting of meglumine, lysine, sodium and potassium citrate and sodium and potassium carbonate, and from the group consisting of magnesium aluminum silicate and talc.

17. The process according to claim 16 wherein the alkaline agent and the adsorbent agent are respectively meglumine and magnesium aluminum silicate.

18. The process according to claim 9 wherein:
the cellulosic polymer is present in the atomized matrix in a proportion ranging from about 30% to about 50% by weight and the methacrylic polymer is present in a proportion ranging from about 10% to about 25% by weight; and
the active ingredient is present in the atomized matrix at a maximum level of about 50% by weight.

19. The process according to claim 18, wherein the proportions of cellulosic and methacrylic polymers in the matrix range respectively from about 40% to about 45% and from about 15% to about 20% by weight, and in that the maximum amount of the active ingredient in the matrix is about 30% by weight.

20. A process for masking the taste of a pharmaceutical product according to claim 1 intended for oral administration in an aqueous suspension, wherein said active ingredient is entrained homogeneously inside a matrix comprising combining at least a cellulosic polymer and a methacrylic polymer with at least an alkaline agent and an adsorbent agent.

* * * * *